(12) United States Patent
Wilson

(10) Patent No.: US 7,188,513 B2
(45) Date of Patent: Mar. 13, 2007

(54) DETECTING CONCEALED SECURITY THREATS

(76) Inventor: Marshall Wilson, 1737 Milford, Houston, TX (US) 77098

( * ) Notice: Subject to any disclaimer, the term of this patent is extended or adjusted under 35 U.S.C. 154(b) by 0 days.

(21) Appl. No.: 11/186,176

(22) Filed: Jul. 21, 2005

(65) Prior Publication Data
US 2006/0226998 A1 Oct. 12, 2006

Related U.S. Application Data

(63) Continuation-in-part of application No. 10/896,397, filed on Jul. 22, 2004.

(51) Int. Cl.
*G01N 35/10* (2006.01)
*G01N 1/24* (2006.01)
(52) U.S. Cl. .................. 73/31.05; 73/31.01; 73/31.03; 73/863; 73/864.81
(58) Field of Classification Search .............. 73/31.01, 73/31.02, 31.03, 31.05, 863, 864.81
See application file for complete search history.

(56) References Cited

U.S. PATENT DOCUMENTS

| H1293 H | 3/1994 | Carlon ........................ 73/23.2 |
|---|---|---|
| 5,440,916 A | 8/1995 | Stone et al. ................ 73/23.31 |
| 5,443,354 A | 8/1995 | Stone et al. ................. 414/729 |
| 5,638,420 A | 6/1997 | Armistead |
| 5,838,759 A | 11/1998 | Armistead |
| 5,859,362 A * | 1/1999 | Neudorfl et al. ............. 73/23.2 |
| 6,047,588 A | 4/2000 | Danilychev .................. 73/23.2 |
| 6,234,006 B1 * | 5/2001 | Sunshine et al. .......... 73/29.01 |
| 6,344,818 B1 | 2/2002 | Markov |
| 6,658,087 B2 | 12/2003 | Chalmers et al. |
| 6,701,772 B2 | 3/2004 | Kreichauf et al. ........... 73/23.2 |
| 2001/0042413 A1 * | 11/2001 | Sakairi et al. ........... 73/863.11 |
| 2002/0078771 A1 * | 6/2002 | Kreichauf et al. ......... 73/866.5 |
| 2003/0085348 A1 * | 5/2003 | Megerle ..................... 250/287 |
| 2003/0108150 A1 | 6/2003 | Klaus-Peter |
| 2003/0201394 A1 | 10/2003 | Peoples ................... 250/336.1 |
| 2004/0015264 A1 * | 1/2004 | Holland et al. ............. 700/225 |
| 2004/0020267 A1 | 2/2004 | Megerle |
| 2004/0226342 A1 * | 11/2004 | Taricco ...................... 73/23.35 |

OTHER PUBLICATIONS

Williams, A. "Trace Chemical Mine Detection Data Collection Final Scientific and Technical Report", Sep. 15, 2003, pp. 1-102.*

* cited by examiner

*Primary Examiner*—Daniel S. Larkin
(74) *Attorney, Agent, or Firm*—Baker Botts L.L.P.

(57) ABSTRACT

Systems, methods and apparatus for detecting concealed security threats by sampling molecules of substances for assessment wherein these molecules may be contained in the air in or near concealed security threats. Inspection of cargo containers by sampling the air contained therein and then analyzing the sampled air from the container for security threats including chemical, biological, radiological, nuclear, and high-explosive threats without requiring the modification of the existing container, the movement of the container to a particular inspection site, and without opening the container. Nuclear security threats may also be scanned for with close proximity nuclear radiation detection sensors closely coupled to areas at or near the concealed security threats. In addition, detection of other types of contraband, including illegal substances, embargoed materials and human and/or animal stowaways may also be assessed. The concealed security threat detection system generally includes a detection system comprising a detector array, an air-moving device, and one or more air-sampling devices. This system may be mounted upon a vehicle for mobility, run on tracks, cables and pulleys, telescoping and swiveling arms, etc.

18 Claims, 12 Drawing Sheets

DETECTING CONCEALED SECURITY THREATS

RELATED PATENT APPLICATION

This application is a continuation-in-part application of and claims priority to commonly owned U.S. patent application Ser. No. 10/896,397; filed Jul. 22, 2004; entitled "Apparatus for Accessing Container Security Threats and Methods of Use," by Marshall Wilson; which is hereby incorporated by reference herein for all purposes.

TECHNICAL FIELD

The present disclosure relates to apparatus and methods for detecting concealed security threats, and, more particularly, to sampling of molecules of substances for assessment wherein these molecules may be contained in the air in or near concealed security threats. More specifically, for example but not limited to, it may relate to a device for the inspection of each individual cargo container by analyzing the air disposed within the container for security threats including chemical, biological, radiological, nuclear, and high-explosive threats without requiring the modification of the existing container, the movement of the container to a particular inspection site, and without opening the container. Nuclear security threats may also be scanned for with close proximity nuclear radiation detection sensors closely coupled to areas at or near the concealed security threats. In addition, detection of other types of contraband, including illegal substances, embargoed materials and human and/or animal stowaways may also be assessed.

BACKGROUND

The global economy depends upon the physical shipment of materials between markets. The scale and pace at which these materials are shipped has exploded in recent years due in part to the invention and proliferation of the intermodal container. Ninety percent of the world's freight now moves in a container. Virtually anyone in the world can arrange with an international shipper or carrier to have an empty intermodal container delivered to their home or workplace. They then could load it with tons of material, declare in only the most general terms what the contents were, "seal" it with a 50-cent lead tag, and send it on its way to any city and town in the United States. The job of transportation providers was to move the box as expeditiously as possible and to exercise care to ensure that the integrity of a container's contents was not compromised.

The responsibility for making sure that goods loaded in a container were legitimate and authorized is shouldered almost exclusively by the importing jurisdiction. However, as the volume of containerized cargo has grown, the number of agents assigned to police that cargo has stayed relatively flat or even declined among most trading nations. The rule of thumb in the inspection business is that it takes five agents three hours to conduct a thorough physical examination of a single full intermodal container. Last year nearly 20 million containers were delivered to America's borders via ship, train, and truck. Approximately 1 to 2 percent of that cargo was actually inspected.

Thus, for would-be terrorists, the global intermodal container system that is responsible for moving the overwhelming majority of the world's freight provides ample opportunity for launching a terrorist attack. The almost complete absence of any security oversight in the loading and transporting of a container from its point of origin to its final destination and the growing volume and velocity at which containers move around the planet creates a daunting problem for inspectors. The use of these containers as a weapon has the potential to halt all shipments of containerized cargo into our ports and across our borders. Consequently, a relatively low cost terrorist attack could result in billions of dollars in losses to the U.S. economy.

Given the current state of container security, it is hard to imagine how a post-event lockdown on container shipments could be either prevented or short-lived. A terrorist could easily use a container as a weapon delivery device, for example, high-explosives such as those used in the attack on the Murrah Federal Building in Oklahoma City, some form of chemical weapon, a bio weapon, a nuclear device or "dirty bomb." All these scenarios are conceivable since the choice of a weapon would not be constrained by any security measures currently in place in seaports or within the intermodal transportation industry.

Conventional devices for inspecting containers generally involve the use of penetrating radiation to detect contraband. For example, U.S. Pat. No. 4,430,568 (Osami Yoshida et al.) describes a package inspection system for automatically inspecting the contents of a package, such as a container, unloaded from a ship without opening or unpacking the container. The device comprises an X-ray transmitter, an X-ray receiver, and a processing unit for image processing. This device relies on a large X-ray unit and requires the container be moved through the unit. Similarly, U.S. Pat. No. 5,638,420 (Armistead) describes a radiographic inspection apparatus for large containers, vehicles and structures having a movable frame, which can straddle the container or object being inspected. The straddling frame has opposed parallel sides, which carry a source of penetrating radiation and a detector array. The source or sources are moved along the length of a container while radiographic image data is being sequentially recorded. While this device does not necessarily require the movement of the container to an inspection site, the straddling frame at least requires some space between containers in which to move. Since containers are often stacked in close proximity, the Armistead device would at least require that some containers be moved prior to inspection. Furthermore, neither of the devices described above provide for the actual detection of chemical or biological contaminants, rather they rely on radiation imaging to detect suspect structures or nuclear materials.

Published U.S. Patent Application No. 2003/0201394 (Peoples) describes a device that detects radiological or chemical contaminants in cargo containers via a detector system mounted upon a spreader bar. The device is capable of sampling air next to an existing opening, such as a vent, in the container or inserting an air sampling probe into a spring loaded door located in the roof of the container. The device described by Peoples centers on the rationale that the container being inspected is in the process of being lifted by the spreader bar and is not in close proximity to other containers. Therefore, any contamination detected in the air adjacent to the container is assumed to emanate from the container being lifted. This device would not provide accurate results if the container were in storage and stacked adjacent to other containers. In addition, the spring loaded door requires the modification of the existing container.

Published U.S. Patent Application No. 2004/0024278 (Megerle) describes a device that samples the air of a container for biological and chemical contaminants. The device is directed toward containers having an air distribution plenum that can establish a flow of air through the container, which is then analyzed for the presence of hazardous materials. Similar to the device described in Peoples, this device also requires the modification of the container by installing a means to distribute an air flow through the container. In addition, the Megerle device requires both an air delivery mechanism and an air collection mechanism since the system relies upon a positive pressure source for its air supply. Other security threats may be concealed in baggage, briefcases, backpacks, explosive vests, etc.

SUMMARY

Specific example embodiments of apparatus and methods disclosed, provide for inspection of concealed security threats, e.g., individual cargo containers, baggage, briefcases, backpacks, explosive vests, thermos bottles, etc. These specific example embodiments may be capable of analyzing molecules contained in the air disposed within a container (e.g., cargo container, baggage, briefcase, backpack, explosive vest) and/or around the container for security threats including chemical, biological, radiological, nuclear, and high-explosive threats. In addition, specific example embodiments, according to the present disclosure, may also be used to detect other types of contraband, including illegal substances, embargoed materials, hazardous industrial materials, chemical vapor or material, and human and/or animal occupancy of the container, such as by sensing carbon dioxide concentration or by auditory means.

Specific example embodiments, according to the present disclosure, may also be useful for analyzing the molecules contained in the air within any contained space, such as railroad boxcars, aircraft passenger, cargo, and luggage compartments, liquid cargo containers such as tank cars, tractor trailers, ships, and storage tanks. The device generally comprises a vent cup mounted upon a telescoping actuator. The vent cup is designed to mate with the standard vents installed upon various cargo containers, thus may be manufactured in various shapes and sizes. For example, the vent cup for mating to a standard TC 104 container may be generally rectangular in shape and designed to fit against the vent. Generally, the vent cup comprises an outer shell defining an interior space into which an air sample will be drawn. The outer shell has a leading edge surrounding the interior space that mates with the wall of the container. A seal is disposed along the leading edge to ensure that the air located within the container is drawn into the vent cup. The seal may be manufactured of a rubber, foam, or any suitable pliable and conforming material, so that it may conform to any irregularities in the container wall. Alternatively, the seal may be in the form of an inflatable bladder, which may also conform to the shape of the container wall.

The outer shell of the vent cup may also comprise an air duct that connects the vent cup to an air-moving device, such as a vacuum pump, air compressor, or similar device, which pulls the air from within the container into the vent cup and through the air duct. If an inflatable bladder is used as the vent cup seal, the air-moving device may comprise a reversible motor such that the air-moving device can be employed to inflate the bladder as necessary. The air duct connecting the vent cup to the air-moving device travels along the length of the telescoping actuator holding the vent cup and terminates at the air-moving device, which may discharge into an air distribution manifold. In addition, a Venturi based vacuum generator may be used so that only one motor is required. The Venturi based vacuum generator system may allow for inflating and deflating an air bladder, and suction of air into a manifold with only the action of a solenoid controlling the flow of air.

The air distribution manifold may be coupled to a detection system, comprising a plurality of individual detectors capable of detecting chemical and high-explosive agents, biological agents, radiological agents, and nuclear material (e.g., molecules thereof). The entire system may be mounted upon a mobile platform, which may be placed within close proximity to a container while the container is in storage, being rearranged or moved, or while the container is in place upon the vessel, truck, plane, or railcar on which it was shipped. The mobile platform may also be equipped with a control mechanism for extending and retracting the telescoping actuator in order to position the vent cup and seal it against the vent of the container from which the air is to be sampled.

The vent cup may also comprise a close proximity sensor, e.g., radiological detection device, such as Geiger counters, ionization detectors, semiconductor diode detectors, scintillation counters, neutron detectors, and the like. In addition, the vent cup may also house any other detector in which proximity to the sample point is important. The system may also comprise a removable, manually telescoping wand that may also be connected to the air-moving device. When a wand is employed, the suction port of the air-moving device may be manifolded such that either the wand or the vent cup is selectable as a means to sample the air within a container. The suction end of the wand may be fitted with a crevice tool that may be positioned adjacent to, or inserted into, any opening or crack in the container shell when a vent is inaccessible. Like the air duct of the vent cup, the discharge end of the wand may be routed through the air-moving device, into the air distribution manifold and into the detection system.

A mobile inspection apparatus for sampling air within a container, according to a specific example embodiment of this disclosure, comprises: an air sampling device for withdrawing an air sample from within the container; an air moving device having a suction port and a discharge port; a conduit connecting the air sampling device to the suction port of the air moving device such that when the air moving device is operating, air is pulled into the air sampling device from the container; and a detector array having an air distribution manifold connected to the discharge port of the air moving device for receiving the air sample and distributing the air sample to a plurality of individual detectors housed within the detector array. The mobile inspection apparatus may be mounted upon a vehicle. The vehicle may provide power to the mobile inspection apparatus. The mobile inspection apparatus may be mounted upon an all-terrain vehicle. The air sampling device may further comprise a means for taking an air sample from the container through a vent having one or more openings. The means for taking an air sample from the container through the vent may comprise a housing that fits over the one or more openings in the vent. The housing further may comprise a sealing member connected to the housing and disposed between the housing and the container. The housing may be mounted upon a telescoping arm. The mobile inspection apparatus may further comprise a control mechanism for positioning the telescoping arm. The mobile inspection apparatus may further comprising a DC power supply for a supplying power to the mobile inspection apparatus. The mobile inspection apparatus may further comprise a secondary air sampling device and a second conduit connecting the secondary air sampling device to the suction port of the air moving device. The suction port of the air moving device may comprise a means for selecting one of the air sampling devices from which an air sample is taken. The secondary air sampling device may comprise a crevice tool for taking air samples via small openings in the container. The detector array may comprise a plurality of sensors for sensing chemical, biological, radiological, nuclear, and high explosive materials. The detector array may comprise a plurality of sensors for sensing illicit drugs, hazardous industrial materials, and chemical vapors and materials. The detector array may comprise a plurality of sensors for sensing human occupancy within a container.

A method for inspecting the air within a container having a vent with one or more openings, according to another specific example embodiment of this disclosure, comprises the steps of: providing a mobile inspection apparatus comprising an air sampling device for withdrawing an air sample from within the container, an air moving device having a suction port and a discharge port, a conduit connecting the air sampling device to the suction port of the air moving device such that when the air moving device is operating, air is pulled into the air sampling device from the vent, and a detector array having an air distribution manifold connected to the discharge port of the air moving device for receiving the air sample and distributing the air sample to a plurality of individual detectors housed within the detector array; positioning the air sampling device adjacent to the vent; operating the air moving device to pull an air sample from the vent and to discharge the air sample into the detector array; and having the air sample analyzed by the plurality of individual detectors in the detector array.

A method for inspecting the air within a container having a closed aperture with a door defining a small space between the door of the closed aperture and the container wall, according to yet another specific example embodiment of this disclosure, comprise the steps of: providing a mobile inspection apparatus comprising an air sampling device having a crevice tool for withdrawing an air sample from within the container, an air moving device having a suction port and a discharge port, a conduit connecting the air sampling device to the suction port of the air moving device such that when the air moving device is operating, air is pulled into the air sampling device from the container via the crevice tool, and a detector array having an air distribution manifold connected to the discharge port of the air moving device for receiving the air sample and distributing the air sample to a plurality of individual detectors housed within the detector array; positioning the crevice tool within the small space between the door of the closed aperture and the container wall; operating the air moving device to pull an air sample from the container and to discharge the air sample into the detector array; and having the air sample analyzed by the plurality of individual detectors in the detector array. The crevice tool may be mounted upon a telescoping arm.

BRIEF DESCRIPTION OF THE DRAWINGS

A more complete understanding of the present disclosure and advantages thereof may be acquired by referring to the following description taken in conjunction with the accompanying drawings wherein.

Figure 1:
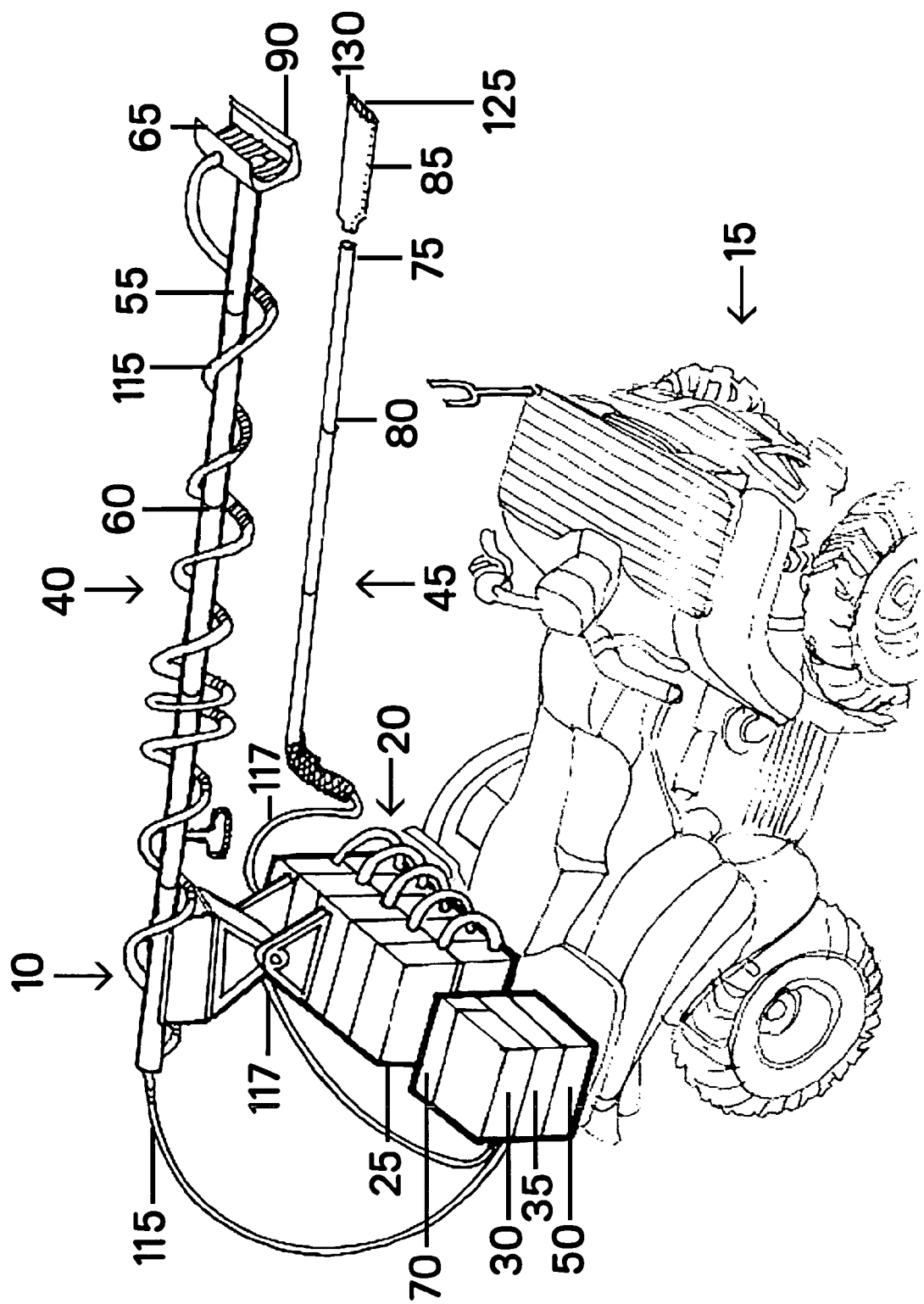
FIG. 1 illustrates a mobile container inspection device mounted upon an all-terrain vehicle, according to a specific example embodiment of the present disclosure.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

Referring now to the drawing, the details of specific example embodiments are schematically illustrated. Like elements in the drawings will be represented by like numbers, and similar elements will be represented by like numbers with a different lower case letter suffix.

Referring to FIG. 1, depicted is a mobile container inspection device mounted upon an all-terrain vehicle, according to a specific example embodiment of the present disclosure. The detection system 10 may be mounted upon an all-terrain vehicle (ATV) 15. Alternatively, the detection system 10 may be mounted upon any vehicle, trailer or man carried. The detection system 10 comprises a detector array 20, a detector array plenum 25, an air-moving device 30, a primary mover 35, a primary air sampling device 40, and a secondary air sampling device 45. The detection system 10 may be mounted on the front or rear rack of the vehicle 15. The detection system 10 may draw power from the electrical system powering vehicle 15, or alternatively, a DC power supply 50, such as a battery pack, may also be mounted upon vehicle 15.

Considering the detection system 10 in more detail, primary air sampling device 40 is shown in its retracted configuration. Primary air sampling device 40 comprises a vent-mating end 55 mounted upon a telescoping actuator 60. The vent-mating end 55 is designed to mate with the standard vents installed upon various cargo containers, thus may be manufactured in various shapes and sizes. In the embodiment illustrated in FIG. 1, the vent-mating end 55 takes the form of a vent cup 65 that mates to a standard TC 104 container, thus has a generally rectangular shape. The telescoping actuator 60 is coupled to a control panel 70. Control panel 70 comprises automatic controls, which may include horizontal, vertical, extension and retraction controls, which move the primary air sampling device 40 into position to mate with the vent of a cargo container. Control panel 70 may also have manual controls.

In addition to the primary air sampling device 40, detection system 10 may also comprise a secondary air sampling device 45. Similar to primary air sampling device 40, the secondary air sampling device 45 comprises an air-sampling end 75 mounted upon a telescoping actuator 80. The telescoping action of the secondary air sampling device 45 is performed manually. The air sampling end 75 of secondary air sampling device 45 comprises an interchangeable crevice tool attachment 85 that is capable of being placed adjacent to or inserted into cracks formed by the doors of the container, or any other apertures that may be present on the container or contained air space.

Figure 2:
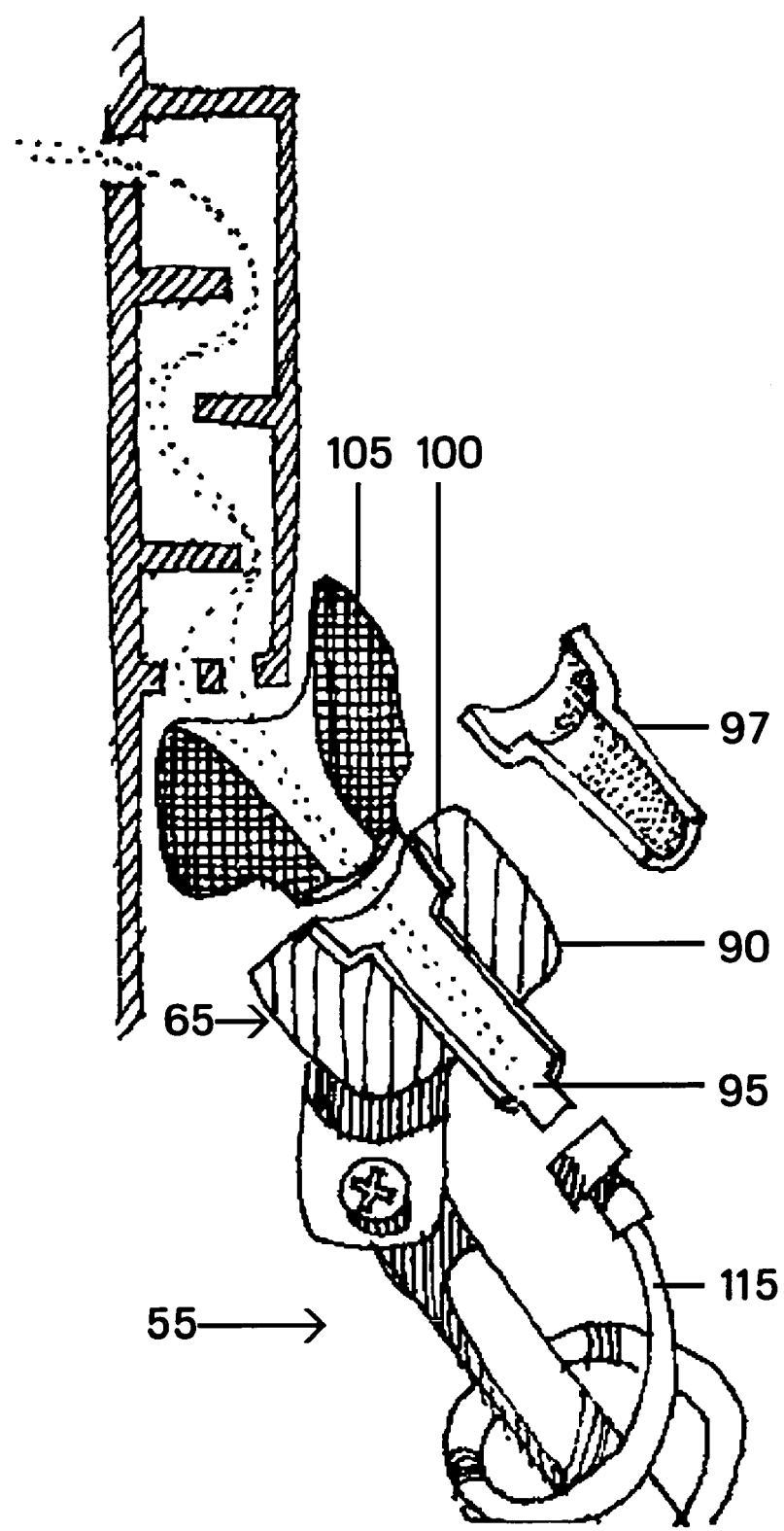
FIG. 2 illustrates a vent cup for mating to a TC 104 container having a foam seal, according to a specific example embodiment of the present disclosure.

Referring to FIG. 2, depicted is a vent cup for mating to a TC 104 container having a foam seal, according to a specific example embodiment of the present disclosure. FIG. 2 illustrates the vent-mating end 55 of primary air sampling device 40 in more detail. In FIG. 2, the vent-mating end 55 may take the form of a vent cup 65 that mates to a standard TC 104 container, thus the vent cup 65 may have a generally rectangular shape and dimensions slightly larger than the TC 104 vent. The vent cup 65 comprises an outer shell 90 defining an interior space 95 into which an air sample will be drawn. The vent cup 65 may also contain a replaceable insert 97 that fits within interior space 95 for ease of maintenance. The outer shell 90 has a leading edge 100 surrounding the interior space 95 that mates with sealing member 105 that communicates with the wall of the container being sampled. The sealing member 105 may be manufactured of a rubber or foam, or any other suitable pliable and conforming material, so that it conforms to any irregularities in the container wall.

Alternatively, the sealing member 105 may be in the form of an inflatable bladder, which can also conform the shape of the container wall. The inflatable bladder may utilize a separate connection to the air-moving device 30, such that air-moving device 30 may be employed to inflate and deflate inflatable bladder.

In addition, vent cup 65 may also comprise a radiological detection device, such as Geiger counters, ionization detectors, semiconductor diode detectors, scintillation counters, neutron detectors, or any other detector where proximity to the sample point is important.

Referring back to FIG. 1, the air sampling end 75 of the secondary air sampling device 45 comprises a crevice tool attachment 85 that may be used on either telescoping arm 40 or 45. The leading edge 125 of crevice tool attachment 85 comprises a knife like portion 130 that can be used to pry open a crack between the container and a door or other aperture and to slide between any seal that may be present. Air duct 117 connects the secondary air sampling device 45 to air-moving device 30.

The outer shell 90 of the vent cup 65 also comprises an air duct 115 that connects the vent cup 65 to the air-moving device 30, such as a vacuum pump, air compressor, or similar device, which pulls air from within the container into the vent cup 65 and through the air duct 115. Air moving device 30 is powered by primary mover 35, e.g., an electric motor, gasoline or diesel engine, etc. If the inflatable bladder is used as the sealing member 105, primary mover 35 may be a reversible motor such that the air-moving device 30 may be employed to inflate the bladder as necessary.

The air duct 115 connecting the vent cup 65 to the air-moving device 30 travels along the length of the telescoping actuator 60 holding the vent cup 65 and terminates at the air-moving device 30, which discharges into detector array plenum 25. Detector array plenum 25 is coupled to detection array 20, which comprises a plurality of individual detectors capable of detecting chemical and high-explosive agents, biological agents, radiological agents, and nuclear material, as well as other types of contraband such as illegal substances, embargoed material or stowaways. Detector plenum 25 may be designed to feed each of the plurality of individual detectors concurrently or, alternatively, detector plenum 25 may comprise a valving arrangement that permits the user to select which detectors are to be utilized for a particular air sample.

Considering the detector array 20 in more detail, the array may house any sensor capable of detecting chemical and high-explosive agents, biological agents, radiological agents, and nuclear material, as well as other types of contraband such as illegal substances, embargoed material, controlled substances or stowaways. The, sensors could include the Joint Biological Point Detection System (JB-PDS) manufactured by Intellitec of Jacksonville, Fla., designed to detect and identify a plurality of biological pathogens. The sensors may also include other similar types of fully-integrated, detecting and identifying biological agent sensors, utilizing automated immunoassay methods, that include the 4WARN manufactured by General Dynamics Canada of Calgary, AB, Canada; Portal Shield or JBREWS manufactured by Sentel of Alexandria, Va.; or others. Some sensors could also take the form of a PCR-Nucleic Analysis system such as those manufactured by Cepheid of Sunnyvale, Calif., or Idaho Technologies of Salt Lake City, Utah. Some sensors could also take the form of detectors that serve only to detect the presence of biological material in particles in the analyzed air stream, like the BIONI, manufactured by Pacific Scientific Instruments of Grant's Pass, Oreg.; the Biological Aerosol Warning System Tier III developed by MIT Lincoln Laboratories in MA; the UV-APS, manufactured by TSI Inc. of St. Paul, Minn.; the UV-FLAPS and BARTS manufactured by General Dynamics Canada of Calgary, AB, Canada; or others. The sensors could also include a particle detector based system like the Biological Aerosol Warning System Tier I, manufactured by Lockheed Martin of Manassas, Va.

In addition, a simple collector, such as a filter or a BioCapture system manufactured by Mesosystems, Inc of Kennewick, Wash.; or other type of particle capture device could also be part of the sensor suite. Such a unit would be intended to capture particles for later laboratory analyses including culturing, immunoassay, and PCR-nucleic acid methods. Such a unit would also be useful for forensic purposes and for the collection of evidence. The sensor suite could also include one or more chemical warfare agent sensors such as ion mobility spectrometers including the ChemPro 100 or the M-90 manufactured by Environics Oy of Mikkeli, Finland, or similar sensors manufactured by Graseby Ionicics and ETG; surface acoustic wave sensor based devices including the JCAD sensor, manufactured by BAE Systems of San Antonio, Tex.; the HAZMATCAD, manufactured by Microsensor Systems Inc. of Bowling Green, Ky.; the Micro Chem Lab on a Chip manufactured by Sandia National Laboratories in Albuquerque, N. Mex.; the SnifferSTAR sensor manufactured by Lockheed Martin of Manassas, Va. and Sandia National Laboratories, or others. They could also take the form of explosives sensors, such as those manufactured by Ion Track Instruments of MA or Smith's Sensors of NJ (formerly Barringer), or contraband drugs sensors manufactured by the latter two manufacturers. The sensors could also include sensors for radiological particles in air, including Geiger counters and other radiological detectors, such as broad beam single scintillation detectors, narrow beam single scintillation detectors, dual scintillation detectors and neutron detector arrays.

In addition to the plurality of detectors housed within detector array 20, the array 20 would also include a means to communicate the readings from the components of the detection array 20 to the user, such as an audible alarm system or an on-board computer that displays the results gathered from the various detector components.

Figure 3:
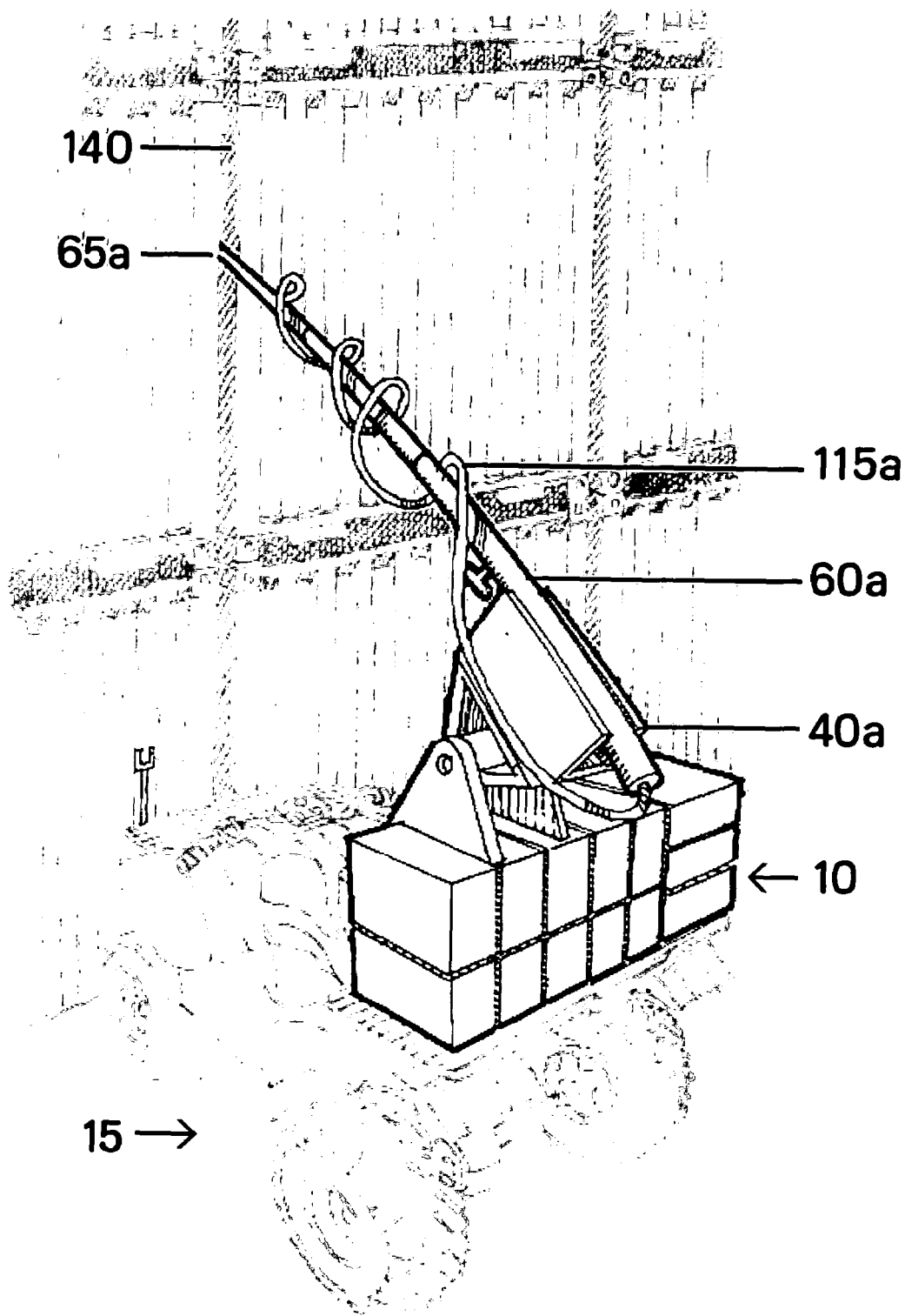
FIG. 3 illustrates a mobile container inspection device mounted upon an all-terrain vehicle employing a collection device having a vent cup pressed against an air vent by an inflation bladder, according to a specific example embodiment of the present disclosure.

Referring to FIG. 3, depicted is a mobile container inspection device mounted upon an all-terrain vehicle employing a vent cup pressed against an air vent by an inflatable bladder and adapted for taking an air sample, according to a specific example embodiment of the present disclosure. The entire detection system 10 may be mounted upon a vehicle 15, which may be placed within close proximity to a container 140 while it is in storage or while it is in place upon the vessel, truck, plane, or railcar in transit. FIG. 3 illustrates the use of the detection system 10 to sample the air within a standard TC 104 container 140 when containers are stacked in close proximity. The air sampling device 40a has been fitted with a vent cup attachment 65a (not shown). The user pilots the vehicle 15 within close proximity to the container 140 and utilizes the automatic controls 70 to extend the telescoping actuator 60a into position. The vent cup attachment 65a is positioned between containers and may be located adjacent to the vent of the container 140 or adjacent to or inserted in a crack in the container wall. The primary mover 35 is engaged and air-moving device 30 begins to pull air from within container 140 through air duct 115a, and into detector array plenum 25 and detector array 20. The vent cup attachment 65a may be held against an air vent of the container 140 with an inflatable bladder (not shown).

Figure 4:
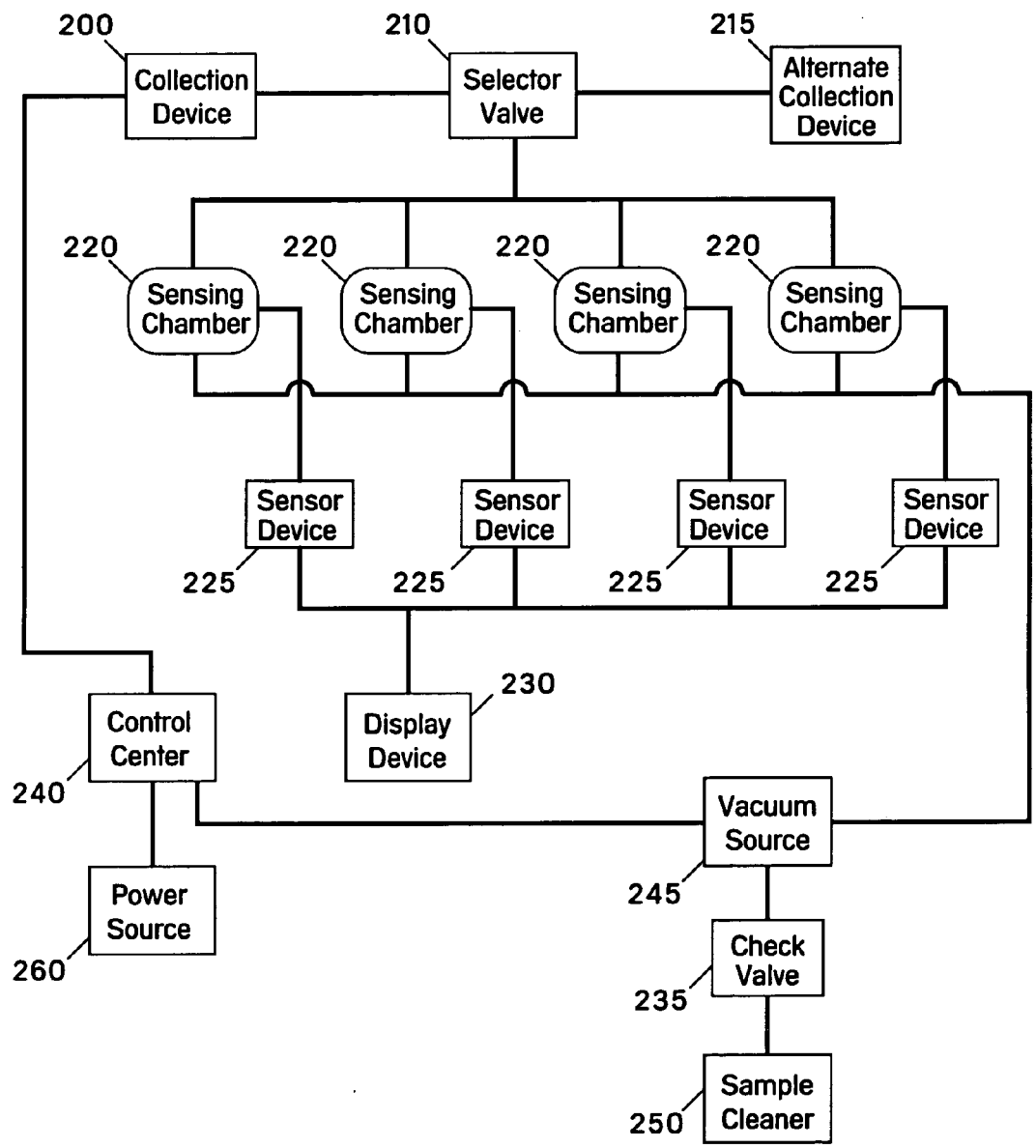
FIG. 4 illustrates a schematic diagram of a detector array and peripheral equipment, according to a specific example embodiment of the present disclosure.

Referring to FIG. 4, depicted is a schematic diagram of a detector array and peripheral equipment, according to a specific example embodiment of the present disclosure. An air sample is collected with either collection device 200 or alternate collection device 215, which may be either the vent cup mounted upon the telescoping actuator or the crevice tool mounted upon the manual sample collecting device as described above. The sample is collected by engaging vacuum source 254, which may be a compressor, vacuum pump, or the like, which reduces the system pressure below atmospheric pressure and causes the air sample to be drawn into the appropriate collection device. Selector valve 210 is positioned with the flow stream between collection device 200 and alternate collection device 215 such that either collection device 200, 215 is individually operable. From selector valve 210, the air sample proceeds through a distribution manifold (not shown) and into a plurality of sensing chambers 220 for the detection of chemical, biological, radiological, nuclear, high explosive threats, as well as other types of contraband, including illegal substances, embargoed materials, hazardous industrial materials, chemical vapor or material, and human occupancy of the container. Each sensing chamber 220 is coupled to conventional electronic sensor output devices 225 that will provide the results of the analyses for each sensing chamber 220. The sensor output devices 225 are coupled to display device 230, which may be an on-board computer and/or printer. The control center 240 provides controls for all electrical and mechanical devices, which are supplied power via power source 260.

After the air sample is analyzed in sensing chambers 220, the air sample completes its flow stream by discharging from vacuum source 245. A check valve 235 in the discharge prevents backflow into the detection system. After being discharged, the air sample may be filtered, combusted, and/or scrubbed in device 250 to prevent contaminated air from being discharged into the environment.

Figure 5:
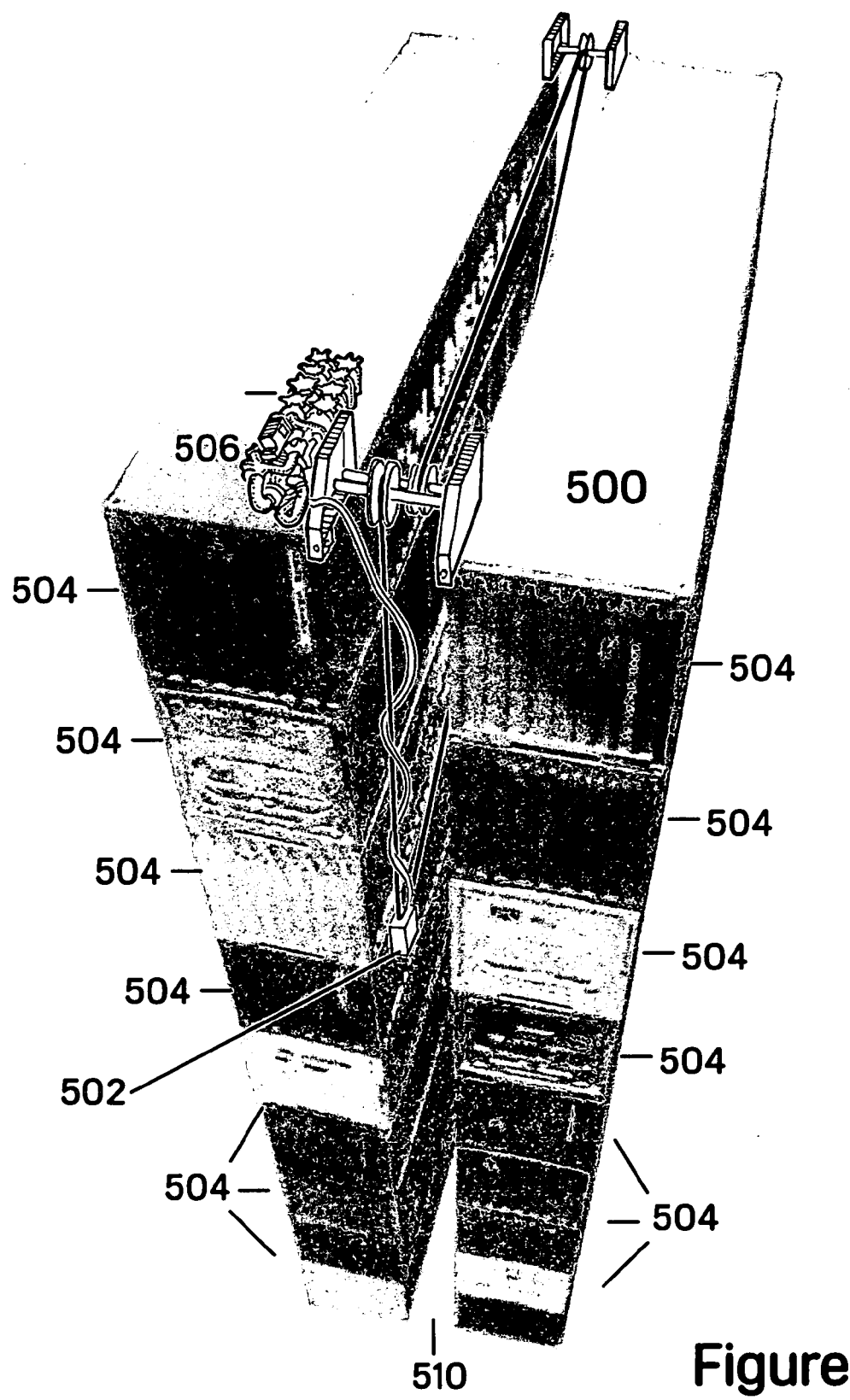
FIG. 5 illustrates a schematic perspective view of a cable access system adapted for moving sensors and/or collection devices into a gap between containers, according to a specific example embodiment of the present disclosure.

Referring now to FIG. 5, depicted is a schematic perspective view of a cable access system adapted for moving sensors and/or collection devices into a gap between containers, according to a specific example embodiment of the present disclosure. The cable access system, generally represented by the numeral 500, moves the sensors and/or collection devices 502 between a plurality of containers 504. Gaps 510 exist between each stack of containers 504. The cable access system 500 may be mounted on one container 504 or straddle adjacent containers 504 at each end of topmost ones of the containers 504 with, for example, a bayonet locking mechanism onto the corner castings of the topmost ones of the plurality of containers 504.

A detection system 506 may be coupled to the sensors and/or collection devices 502 through signal cables and/or air tubing, respectively. The sensors may detect, for example but not limited to, radiation, chemical, biological, etc. The non-radiation (e.g., nuclear) sensors may be located at either the sensors 502a or at the detection system 506. When the sensors are located at the detection system 506, air samples are conveyed from the collection device 502b (similar to the air sampling device 40a of FIG. 3).

A pole or stick have a telescoping feature (not shown) may be used instead of the cable pulley system as used in the cable access system 500. The detection system 506 may be attached to the telescoping pole or stick, e.g., see FIG. 3.

The containers 504 may be stacked up to 13 deep below deck and 11 above the deck of an 18,000 TEU cargo container carrier ship. Currently, large cargo container carrier ships may hold up to 8024 containers 504. Considering the catastrophic consequences of a nuclear explosion all containers 504 should be inspected at a remote location, therefore the logical place for the inspection is at sea. Additionally, this remote location comprehensive inspection may speedup port processing.

Figure 6:
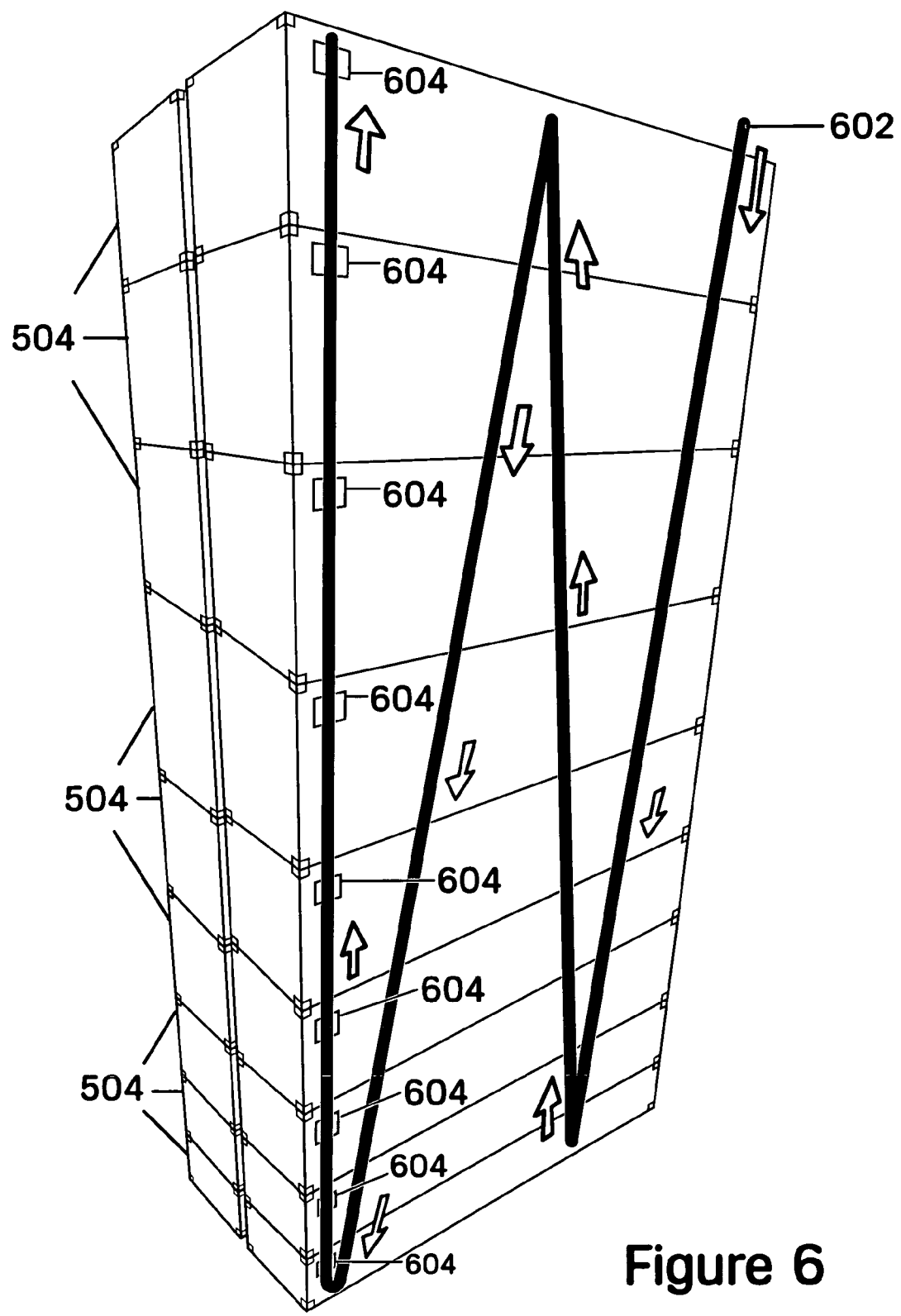
FIG. 6 illustrates a sweep path of a cable system used to move a vent cup and/or close proximity sensor, e.g., radiation sensor, conterminously with each container, according to a specific example embodiment of the present disclosure.

The cable mechanism 500 and the sensors and/or collection devices 502 are adapted so that the containers 504 may be inspected while in place on the cargo container carrier ship. The cable mechanism 500 may move the sensors and/or collection devices 502 between gaps 510 to appropriate areas of the cargo containers 504. FIG. 6 illustrates a sweep path 602 that the cable mechanism 500 may use to move the sensors and/or collection devices 502, e.g., a vent cup 65 having an appropriate contact mechanism, and/or close proximity sensor, e.g., radiation sensor, conterminously with each container 504.

A radiation sensor may be actively monitoring for radiation over the entire sweep path 602. For example, a HPGe Gamma Ray Spectrometer or other radiation detector may be lowered into position in the vertical space 510 between the cargo containers 504, then the sweep path 602 may be used in a search pattern, scanning 18 containers per sweep (nine shown in the FIG. 6 plus nine not shown, on the other side of the gap 510 between the cargo containers 504).

A collection device 502 may take air samples from each vent 604. For example, but not limited to, each vent 604 may be accessed for an air sample on the last trip to the top. The air sample from each of the vents 604 may then be processed in the detection system 506.

A simple "W" path is shown in FIG. 6, however, it is contemplated and within the scope of this disclosure that any path may be taken that would enhance results from a search pattern of the cargo containers 504.

The sensors and/or collection devices 502 may also include a high resolution acoustic sourcing device, e.g., a "thumping" device (not shown). The acoustic sourcing device may be used to vibrate the cargo container 504 so that particles, e.g., molecules, in the air therein may be more reliably sampled. The acoustic sourcing device may cover a wide range of frequencies, from sub-audible to ultrasonic. A blast of air from the device 502 into the cargo container 504 followed by sampling the air may also cause particles to become agitated and thus more reliably sampled. The air samples may be withdrawn from the cargo containers 504 with a negative pressure (suction) from the detection system 506. The sampled air from each of the cargo containers 504 may be analyzed as disclosed hereinabove.

An illumination system and/or video camera may also be included with the sensors and/or collection device 502 so as to more readily identify vent positions, individual container identification, etc. The video camera may also be used to more closely visually inspect a suspect container 504, even when the suspect container is buried under other containers 504.

Figure 7:
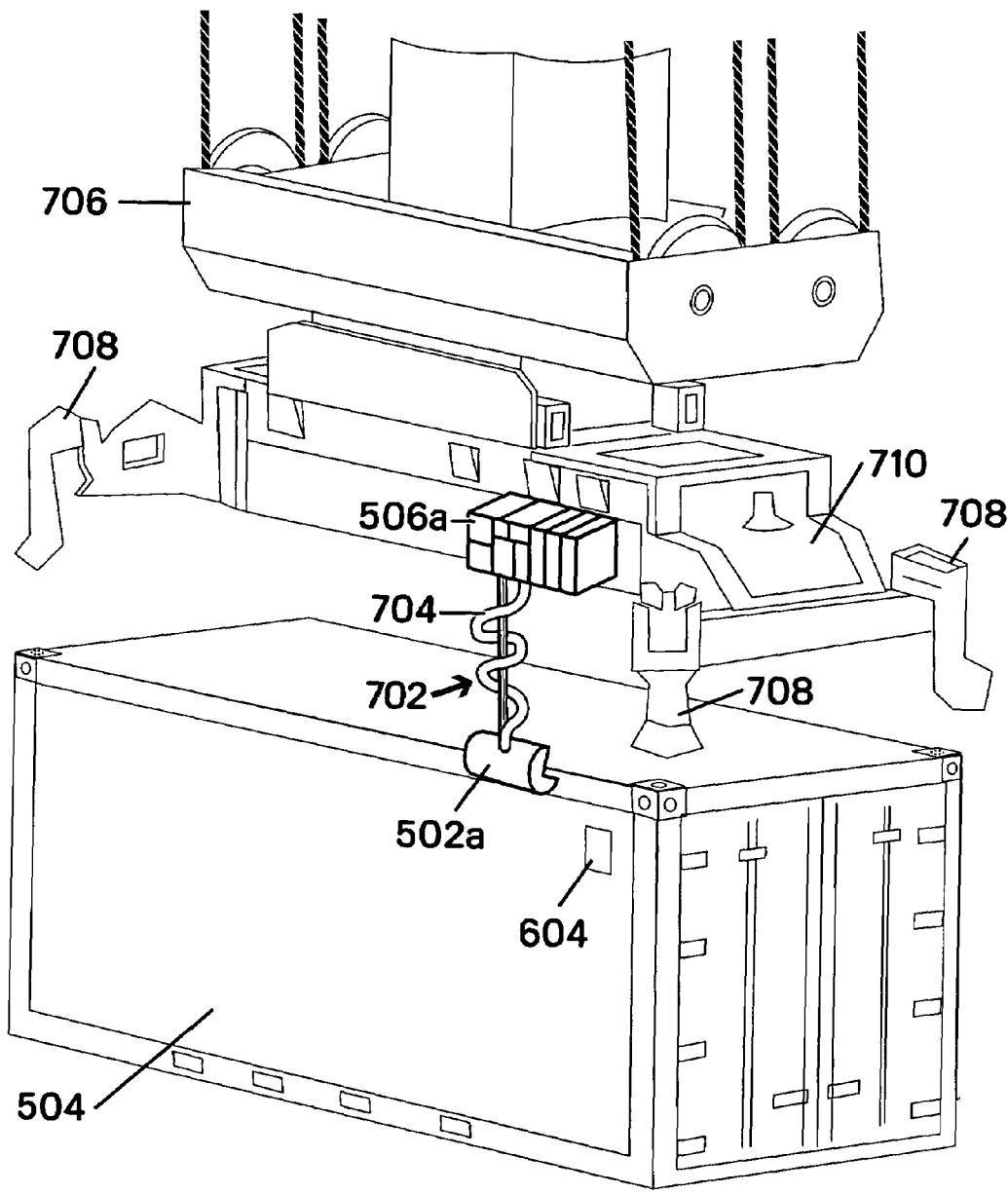
FIG. 7 illustrates a container crane having a mobile container inspection device mounted thereon, according to a specific example embodiment of the present disclosure.

Referring to FIG. 7, depicted is a cargo container crane 706 having a mobile container inspection device 702 mounted thereon, according to a specific example embodiment of the present disclosure. The mobile container inspection device 702 may have a telescoping arm 704 located at the base of a giant seaport cargo container crane 706. A sensor and/or collection device 502a may be attached to the arm 704, and air samples from the container vent 604 may be conveyed to a detection system 506a. The arm 704 may telescope, for example, from about 1 feet to about 15 feet along the length of the cargo container 504 so as to cover areas located on the side of the cargo container 504. The arm 704 may also swivel at the detection system 506a so that substantially the entire side area of the container may be inspected, e.g., nuclear detection, by using sweeping, and/or lateral motions and telescoping of the arm 704. Thus all areas may be traversed of a side of the cargo container 504. The telescoping arm 704 may be mounted on a track that may allow the telescoping arm 704 to traverse the entire side of the cargo container 504.

Each of four twist-locks 708 may engage a container corner casting of the cargo container 504 and then the crane 706 may hoist the container 504 from the cargo container carrier ship to the dock (not shown). A sampling device for a detection system (not shown) may also be attached to a guide or flipper arm which may be adapted for attachment to the twist-lock 708 closest to a vent 604. When the twist-lock 708 closes onto the corner of the container 504, the sampling device may cover the vent 604 and take an air sample therefrom while the remaining open vents may be blocked.

Figure 8B:
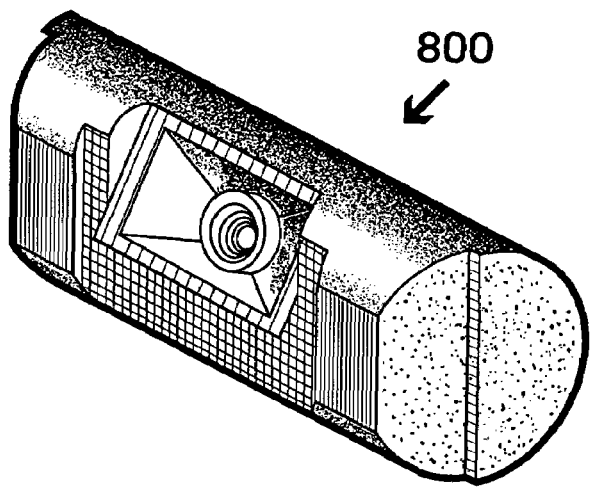
FIGS. 8A, 8B and 8C illustrate various views of a vent cup, according to a specific example embodiment of the present disclosure.
Figure 8A:
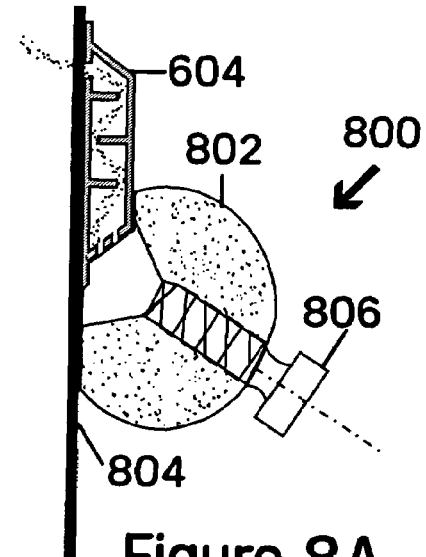
Figure 8C:
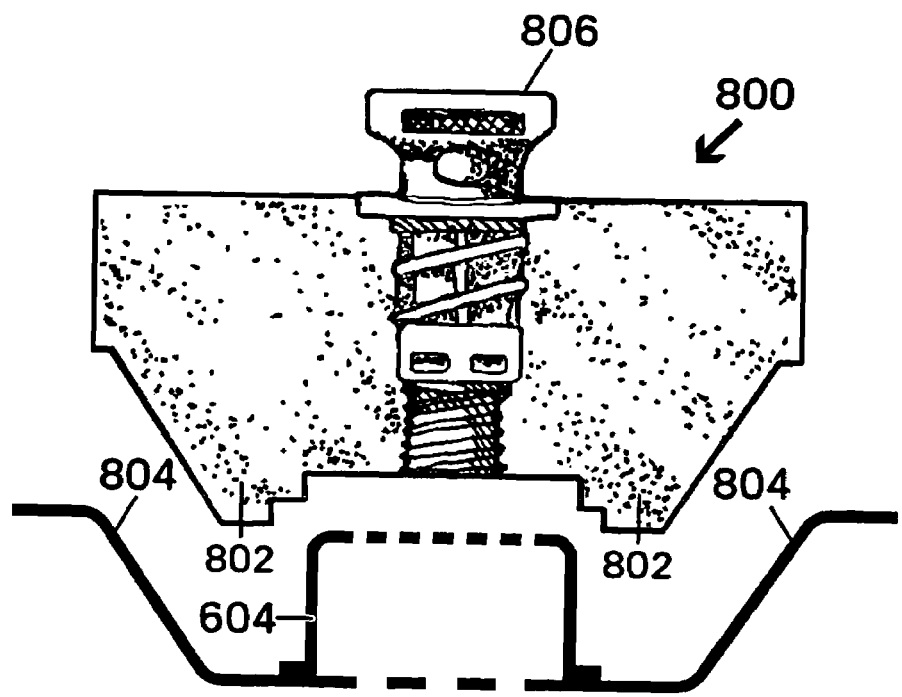

Referring to FIGS. 8A, 8B and 8C, depicted are various views of a vent cup, according to a specific example embodiment of the present disclosure. The vent cup, generally represented by the numeral 800, comprises lips 802 that may be adapted to substantially match the geometry of a container vent 604. In addition, the lips 802 may substantially match the geometry of the folded plate construction of an adjacent wall 804 of the cargo container 504. The lips 802 may be, for example, a hard polyethylene foam material that may align with the folded plate of the adjacent wall 804 of the cargo container 504. Once aligned, the lips 802 may slidingly engage the vent. The polyethylene foam lips 802 may substantially squeeze up against the holes in the vent. A connector 806 may couple the vent cup 800 to the air duct 115 (FIG. 1). The connector 806 may be a "quick connect" style type of air house coupler, as typically used in air operated equipment. The connector 806 may be at an angle with the wall 804 (FIG. 8A).

A small video camera and light source (not shown) for optical observation may be included with the vent cup 800, and may be used for optical container identification and/or sighting purposes for mating the lips 802 with the vent 604.

Figure 9:
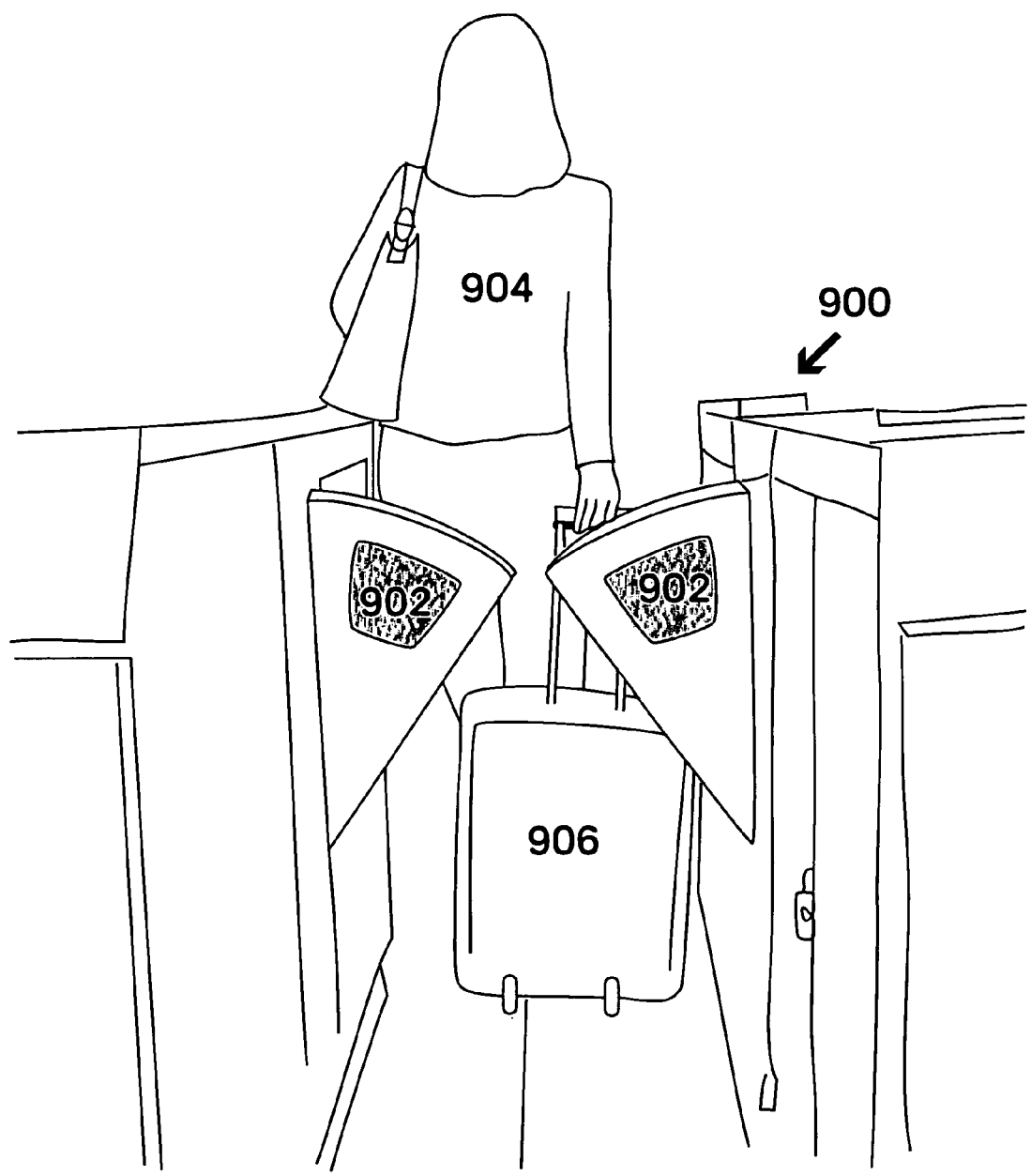
FIG. 9 illustrates a turnstile mechanism enclosure having inspection devices hidden within, according to a specific example embodiment of the present disclosure.

Referring to FIG. 9, depicted is a turnstile mechanism enclosure having an inspection device hidden within, according to a specific example embodiment of the present disclosure. Radiation detection sensors may be placed on either side of the turnstile mechanism enclosure 900 for detection of a suitcase 906. Air sample collection devices may also be placed appropriately in the turnstile mechanism enclosure 900 for taking air samples of the suitcase 906 as it passes by the collection device(s). Sensors and/or collection devices may actuate whenever the turnstile 902 retracts, allowing a person 904 to pass therethrough.

Figure 10:
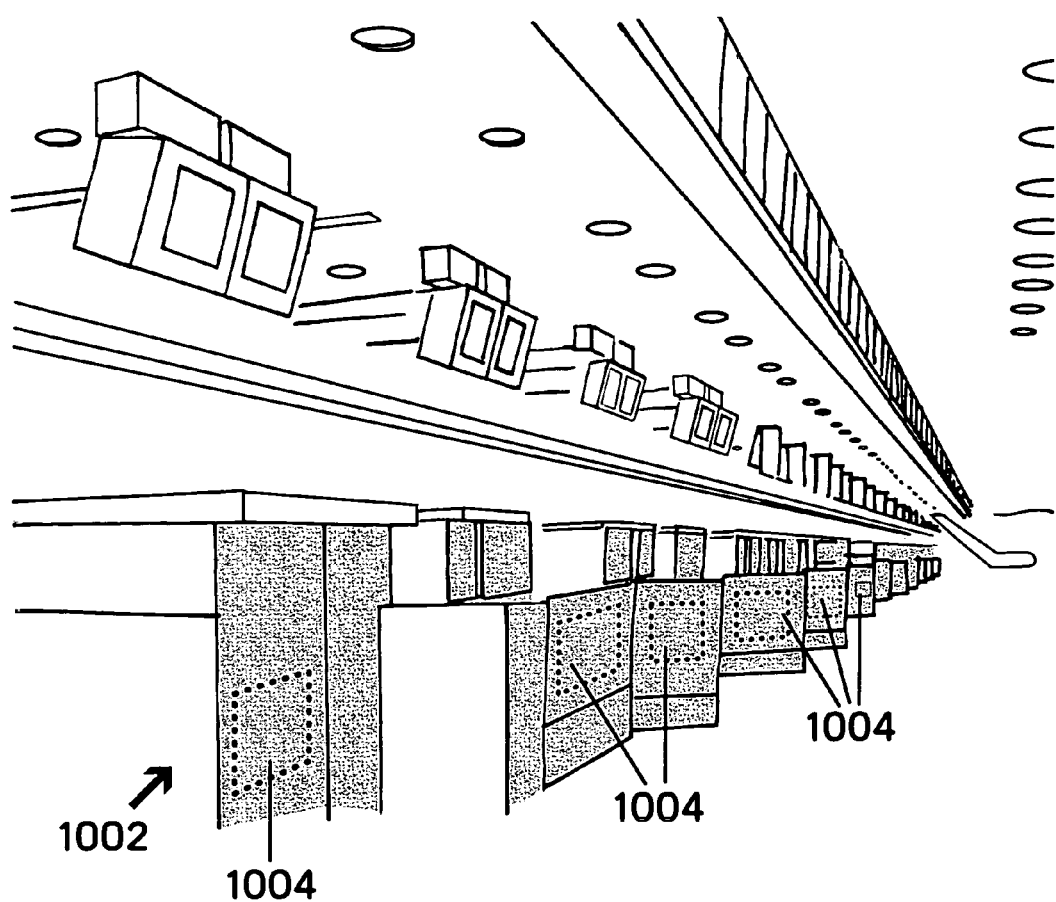
FIG. 10 illustrates check-in counters having inspection devices hidden within, according to a specific example embodiment of the present disclosure.

Referring to FIG. 10, depicted are counters (e.g., check-in counters, customs counters, information counters, money exchange counters, newsstands, bars, food service counters, or any other counter where passengers may linger) having inspection devices hidden within, according to a specific example embodiment of the present disclosure. A counter 1002 may have a vacuum pressure screen (negative pressure) 1004 on a lower front face of the counter 1002 proximate to passengers and their bags. The screen 1004 may deliver air samples to an array of detectors (not shown).

Figure 11:
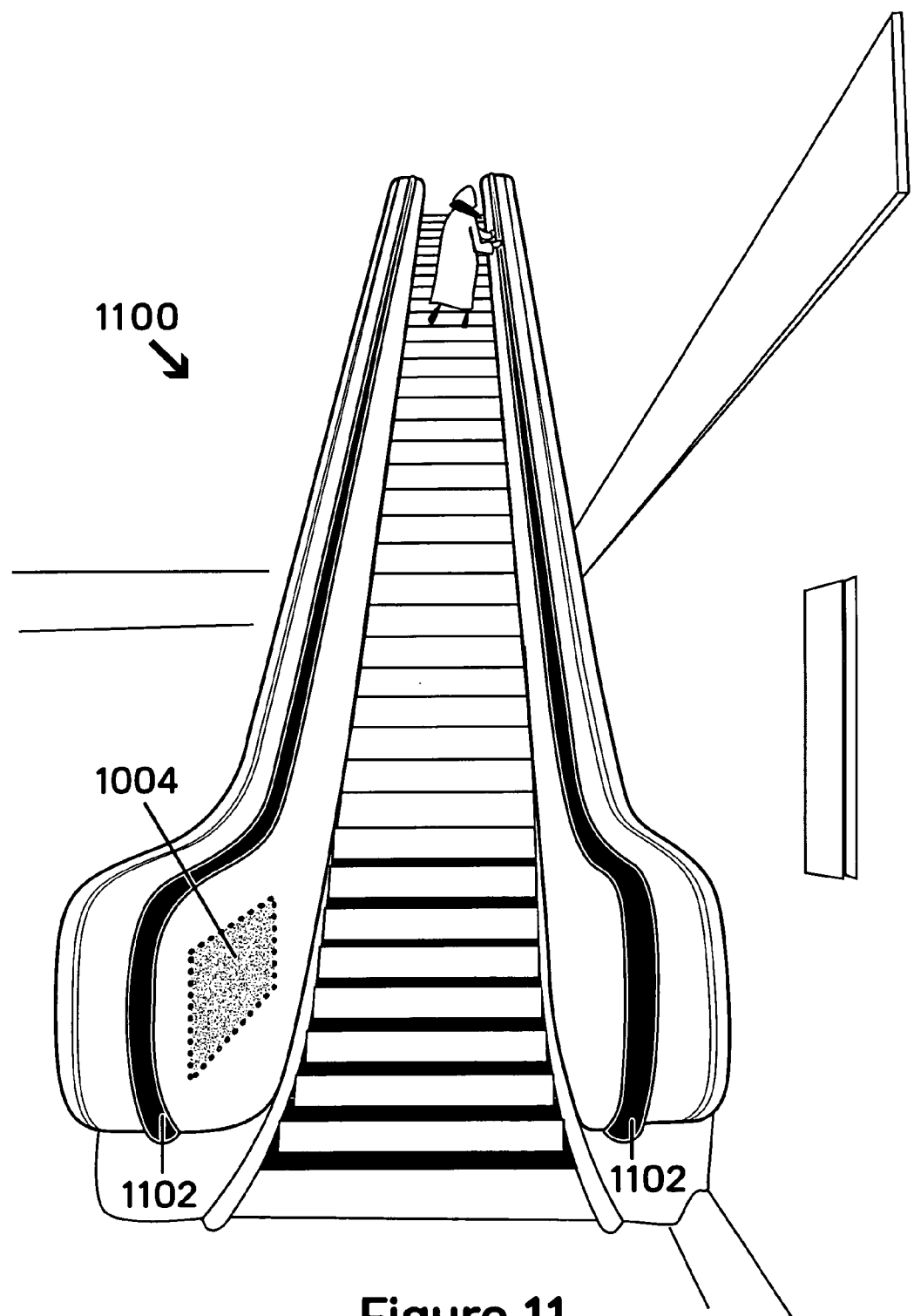
FIG. 11 illustrates an escalator mechanism having inspection devices hidden within, according to a specific example embodiment of the present disclosure.

Referring to FIG. 11, depicted is an escalator mechanism having inspection devices hidden within, according to a specific example embodiment of the present disclosure. The escalator mechanism 1100 may have handrails 1102 that are appropriate for bringing molecules of various substances to an inspection device (hidden) from hand contacts with the handrails 1102. Beyond this point the handrails 1102 may be cleansed. Air sampling and/or radiological samplers/sensors may be located in the side panels of the escalator mechanism 1100. High traffic public spaces use escalators extensively. The escalators are an efficient way of moving large numbers of people around different floor levels. Escalators may be in subways, airports, arenas, stadiums, theaters, public building, etc., all potential targets of terrorists. To change floor levels in these types of buildings everyone, terrorists included, must use the escalators.

A security inspection system as described herein above may have detectors that can operate under cover of the escalator mechanism 1100. Furthermore, the handrails 1102 may bring to the detectors particles (molecules) from contact with persons holding on to the handrail 1102. For example, a continuous handrail 1102 may disappear into the bottom side of the loop in the elevator mechanism 1100, and as the handrail portion having the particles passes a detector array, inspection may proceed. Nuclear sensors may be placed in the walls of the escalator mechanism 1100, and thus be in close proximity to suitcases, brief cases and the like that may be carried by persons using the escalator. In the event that a security threat is identified, coordination with surveillance cameras and gate mechanisms may be used to identify and/or detain suspects riding on the escalator on or about the time the security threat was identified.

Elevators and moving sidewalks (not shown) may also have hidden inspection devices therein, and operate when people riding thereon are in close proximity with the hidden inspection devices.

Figure 12:
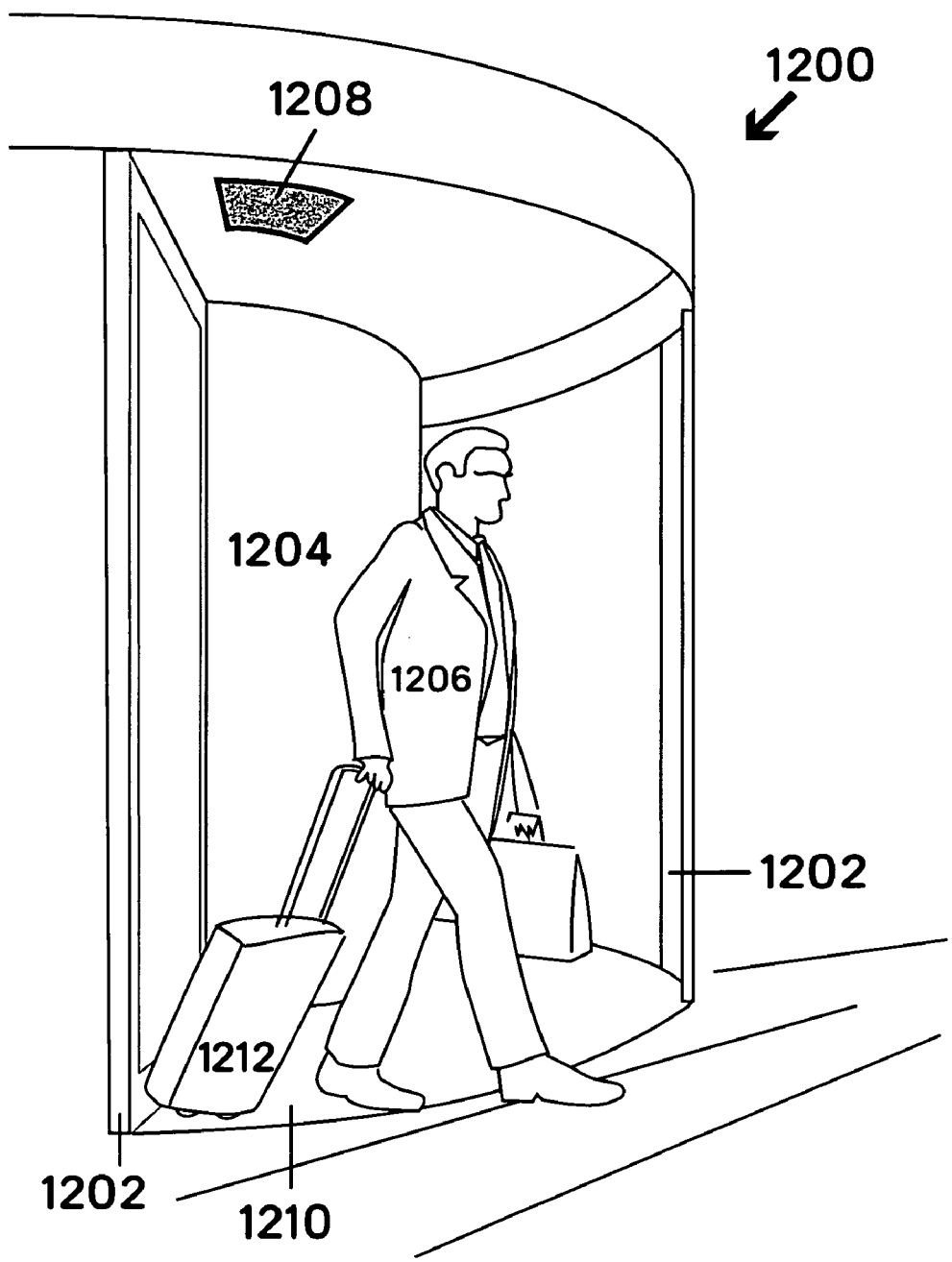
FIG. 12 illustrates a revolving door mechanism having inspection devices hidden in the structure thereof, according to a specific example embodiment of the present disclosure.

Referring to FIG. 12, depicted is a revolving door mechanism having inspection devices hidden in the structure thereof, according to a specific example embodiment of the present disclosure. A revolving door mechanism, generally represented by the numeral 1200, may comprise movable doors 1202 and an opening 1204 through which people 1206 and luggage 1212 may pass through. As people 1206 pass through the opening 1204 between the doors 1202 of the revolving door mechanism 1200, the people 1206 and luggage 1212 will pass under a top portion 1208 and over a bottom portion 1210 of the revolving door mechanism 1200. This allows placement of a security inspection system to be in close proximity to the people 1206 and luggage 1212 for a sufficient time to sense nuclear radiation and/or to take samples of particles (molecules) in the air surrounding the people 1206 and luggage 1212. For example, an air source may be emitted from the floor 1210, pass over the people 1206 and luggage 1212, and then be captured in an air sampling device in the top portion 1208. The locations of the air source and air sampling device may be reversed, e.g., the air source in the top portion 1208 and the air sampling device in the bottom portion 1210.

An important factor in using hidden detectors and air sample collection in the aforementioned turnstiles, check-in counters, escalators and/or revolving doors is secrecy of the security inspections. Hidden surveillance increases the chance of detecting terrorists. By not making security threat surveillance obvious, detection of careless or sloppy potential terrorists may have a higher probability of success. Complete screening may be done on large numbers of people passing through public and private areas. Since turnstiles, check-in counters, escalators and/or revolving doors bring people into close proximity of an enclosed surface(s), more effective particle (molecule) and nuclear detection may be achieved.

It is contemplated and within the scope of this disclosure that data from the detectors, location, time, personal identification information and/or video images of people being inspected may be gathered, transmitted and stored for future reference by police authorities and/or government anti-terrorist agents. Real time correlation of sensor data location, time, personal identification information and/or video images may also be useful for tracking specific incidents, crisis situations and identification of security threats. The sensor information may be sorted into bundles of data, types of data, attributes of data, etc.

Seismic, e.g., three dimensional imaging, and/or ultrasound techniques may be used in detecting a security threat. The seismic and/or ultrasound transmitters and receivers may be placed in areas of ingress and egress, mounted onto mobile inspection systems, etc.

The mobile inspection systems described in FIGS. 1, 3, 5 and 7 may hereinafter be referred to generally as "sensing and detecting mobile platforms (SDMPs). These SDMPs may have an identification serial number and may also have a GPS positioning system for determining the location of the SDMP at any time during storage, transportation and/or use thereof.

Each Sensing and Detecting Mobile Platform may have a variety of detectors, e.g., detectors for Chemical, Biological, Radiological, Nuclear, and Explosive threats, human occupancy, current cargo contained and contraband.

Each Sensing and Detecting Mobile Platform may have a radio frequency identification (RFID) tag, GPS information reader, input pad, and optical camera to establish cargo container identification.

Each Sensing and Detecting Mobile Platform may have a computerized acquisition device, e.g., portable personal computer, for gathering data from the sensing devices. This data may also be stored in the computerized acquisition device.

After gathering data the Sensing and Detecting Mobile Platform may encrypt data in a secure manner and send it by internet, satellite, or an other secure means to a processing center. Upon arriving at the processing center pertinent data may then be directed to the Department of Homeland Security (DHS). Portions of the data may be decrypted, analyzed and/or stored. Appropriate access may be given to private parties for information pertaining to cargo of interest stored in the containers. This cargo information may be stored with associated RFID and GPS information gleaned by the Sensing and Detecting Mobile Platform during inspections of the cargo containers.

Any of the aforementioned security threat detection devices may be located at loading docks, ferry boat docks and ramps, bus terminals, air ventilation ducts, building entrances, parking garage access gates, mechanical access tunnel entrances, moving sidewalks, elevators, escalators; ingress and egress points of buildings, trains, subways, airports, buses and bus stations, etc.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A portable inspection apparatus for withdrawing samples of air from within a plurality of stacked containers and contemporaneously analyzing these air samples for determining a plurality of different security threats, said apparatus comprising:
   an air sampling device adapted for withdrawing samples of air from within a plurality of stacked containers;
   a positioning mechanism moveably coupled to the air sampling device and adapted for positioning the air sampling device proximate to an air vent of each of the plurality of stacked containers, wherein the positioning mechanism comprises at least one cable and at least one pulley;
   a conduit coupled to the air sampling device;
   an air distribution manifold having an inlet coupled to the conduit;
   a plurality of sensors coupled to the air distribution manifold; and
   an air-moving device coupled to an outlet of the air distribution manifold such that when the air moving device is operating the sample of air from a respective one of the plurality of stacked containers is drawn into the air distribution manifold;

whereby the air distribution manifold receives and then distributes to the plurality of sensors the sample of air from the respective one of the plurality of stacked containers;

wherein each of the plurality of sensors detects a different security threat contemporaneously with the withdrawal of the sample of air from within the respective one of the plurality of stacked containers.

2. The portable inspection apparatus of claim 1, wherein the air sampling device further comprises a vent cup adapted for withdrawing the air samples through vents associated with each of the plurality of stacked containers, each of the vents having one or more openings through which passes the air sample.

3. The portable inspection apparatus according to claim 2, wherein the vent cup comprises a housing that fits over the one or more openings in the vents.

4. The portable inspection apparatus according to claim 1, further comprising an illumination device and a video camera for observing an area around the air sampling device.

5. The portable inspection apparatus according to claim 1, further comprising an acoustic source for vibrating each of the plurality of stacked containers so as to agitate particles therein into the air samples taken therefrom.

6. The portable inspection apparatus according to claim 5, the acoustic source is a thumping device.

7. The portable inspection apparatus according to claim 1, further comprising a nuclear sensor attached to the air sampling device.

8. The portable inspection apparatus according to claim 7, the nuclear sensor takes radiation samples while the air sampling device is proximate to each of the plurality of stacked containers.

9. The portable inspection apparatus according to claim 1, wherein the plurality of sensors are selected from the group consisting of sensors for sensing chemical, biological, radiological, nuclear and high-explosive materials; illicit drugs, hazardous industrial materials, and chemical vapors.

10. A portable inspection apparatus for withdrawing samples of air from within a plurality of stacked containers and contemporaneously analyzing these air samples for determining a plurality of different security threats, said apparatus comprising:

an air sampling device adapted for withdrawing samples of air from within a plurality of stacked containers;

a positioning mechanism moveably coupled to the air sampling device and adapted for positioning the air sampling device proximate to an air vent of each of the plurality of stacked containers, wherein the positioning mechanism attaches to at least one of the plurality of stacked containers;

a conduit coupled to the air sampling device;

an air distribution manifold having an inlet coupled to the conduit;

a plurality of sensors coupled to the air distribution manifold; and an air-moving device coupled to an outlet of the air distribution manifold such that when the air moving device is operating the sample of air from a respective one of the plurality of stacked containers is drawn into the air distribution manifold;

whereby the air distribution manifold receives and then distributes to the plurality of sensors the sample of air from the respective one of the plurality of stacked containers;

wherein each of the plurality of sensors detects a different security threat contemporaneously with the withdrawal of the sample of air from within the respective one of the plurality of stacked containers.

11. The portable inspection apparatus of claim 10, wherein the air sampling device further comprises a vent cup adapted for withdrawing the air samples through vents associated with each of the plurality of stacked containers, each of the vents having one or more openings through which passes the air sample.

12. The portable inspection apparatus according to claim 11, wherein the vent cup comprises a housing that fits over the one or more openings in the vents.

13. The portable inspection apparatus according to claim 10, further comprising an illumination device and a video camera for observing an area around the air sampling device.

14. The portable inspection apparatus according to claim 10, further comprising an acoustic source for vibrating each of the plurality of stacked containers so as to agitate particles therein into the air samples taken therefrom.

15. The portable inspection apparatus according to claim 14, the acoustic source is a thumping device.

16. The portable inspection apparatus according to claim 10, further comprising a nuclear sensor attached to the air sampling device.

17. The portable inspection apparatus according to claim 16, the nuclear sensor takes radiation samples while the air sampling device is proximate to each of the plurality of stacked containers.

18. The portable inspection apparatus according to claim 10, wherein the plurality of sensors are selected from the group consisting of sensors for sensing chemical, biological, radiological, nuclear and high-explosive materials; illicit drugs, hazardous industrial materials, and chemical vapors.

* * * * *